United States Patent [19]

Mitani

[11] 4,323,496

[45] Apr. 6, 1982

[54] INNOXIOUS INTERFERON-INDUCING SUBSTANCE, INDUCING AGENT AND PROCESS FOR PRODUCING SAME

[76] Inventor: Ikusaburo Mitani, 46-19, Narashinodai 5-chome, Funabashi-shi, Chiba-ken, Japan

[21] Appl. No.: 134,060

[22] Filed: Mar. 26, 1980

[30] Foreign Application Priority Data

Jul. 14, 1979 [JP] Japan .................................. 54/89463

[51] Int. Cl.³ .............................................. C07G 7/00
[52] U.S. Cl. ............................ 260/112 R; 260/112 B; 260/123.5; 424/85
[58] Field of Search ............. 260/112 R, 112 B, 123.5

[56] References Cited

U.S. PATENT DOCUMENTS

| 1,245,979 | 11/1917 | Satow | 260/112 R X |
| 2,164,284 | 6/1939 | Ralston et al. | 260/112 R X |
| 3,272,640 | 9/1966 | Geurden | 260/112 R X |
| 3,451,990 | 6/1969 | Solé | 260/112 R X |
| 3,501,451 | 3/1970 | Fellers | 260/123.5 X |
| 3,539,549 | 11/1970 | Greenfield | 260/112 R |

*Primary Examiner*—Howard E. Schain

[57] ABSTRACT

Disclosed herein is an innoxious interferon-inducing substance containing neither heteroenzymic proteins and proteins of hetero-arrangement exhibiting the toxicity nor cancerogenic tar substance, but capable of permeating through the cell membrane. Also disclosed are an interferon-inducing agent derived from said substance and a process for producing said substance and said agent.

7 Claims, No Drawings

INNOXIOUS INTERFERON-INDUCING SUBSTANCE, INDUCING AGENT AND PROCESS FOR PRODUCING SAME

This invention relates to an innoxious interferon-inducing substance, or agent and process for producing the same, said interferon-inducing substance containing neither heteroenzymic proteins (abnormal enzyme protein) and proteins of hetero-arrangement (protein of abnormal amino acid sequence) exhibiting toxicity or cancerogenic tar components as the cancerogenic substance, but are capable of permeating through the cell membrane.

Ever since the discovery of an interferon by Isaacs and others, various researches have been made on the interferon which is believed to activate the lymphocyte and macrophage and to impart antitumor activity to cancer cells. To date, however, interferon has not yet been identified and its structural components have not been clarified. Owing to its own toxicity, interferon is not able to permeate through the cell membrane and to directly enter the cells to be built up there. Hence, it is not able to exhibit effective action. The liver and kidney are subjected to considerable load for the detoxication of the interferon and to consume the precious essential amino acids. Further, the heretofore known interferon still involves problems with regard to its continuous dose and its stability. Since only human serum is principally employed as the starting material for the production of the interferon, the production quantity of the interferon is rather limited. Moreover, the range of immunity is also limited because the interferon lacks such an essential protein as a chromoprotein.

In recent years, considerable importance has been given to research for administering an interferon-inducing substance so as to induce the interferon. However, the interferon-inducing substance known to date involves various drawbacks. First, the inducing mechanism has not yet been clarified. Second, the inducing substance is not able to permeate through the cell membrane due to its toxic inclusions (e.g. heteroenzymic proteins, proteins of a hetero-arrangement and cancerogenic substances such as cancerogenic tar components). Hence, it is not able to directly enter the cell and to be deposited therein to provide an effective action. Further, the remedy for the predisposing cause of the disease is not possible. The liver and kidney are subjected to considerable load for detoxication and to consume precious essential amino acids. The inducing substance further produces adverse effects, and its production quantity is limited.

Leukocytic proteins have conventionally been employed as the starting material for the inducing substance. The proteins of this kind are beleived to be mixed proteins of those after the detoxication by the liver of the proteins contained in foodstuffs and those containing toxic proteins that are absorbed by the intestinal tube and pass through the vena portae before reaching the liver.

Since the above-mentioned protein does not permeate through the cell membrane, the protein induces the inducing substance of the interferon by means of Sendai virus or Newcastle virus without relying on human DNA. However, the number of antigens is limited and the range of the inducing substances corresponding to the antigens is extremely narrow. Hence, the range of correspondence is narrow with respect to the antigens which would presumably number as great as tens of thousands.

Moreover, it takes an extended period of time before the inducing substance is produced as a commercial product. Confirmation of its efficacy remains at a level of primary skin experimentation. As the inducing proteins, such as virus, would probably contain heteroenzymic proteins and proteins of a hetero-arrangement, toxicity of the medicament is believed to be extremely high.

The present invention is an innoxious interferon-inducing substance containing at least one member selected from the following three kinds of protein (hereinafter referred to as "MIT") type substances, i.e., conjugated, innoxious, essential proteins, MIT protein derivatives derived from said MIT and MIT-derived proteins derived from said MIT, and capable of permeating through a cell membrane. The MIT contains at least one conjugated protein selected from glycoproteins, nucleoproteins, chromoproteins and phosphoroproteins each of which contains a conjugated, innoxious, essential amino acid (hereinafter referred to as "MIT amino acid") which is levo-rotatory and contains no cancerogenic tar component, heteroenzymic protein and protein of hetero-arrangement. The MIT is capable of being an interferon-inducing substance by acting on DNA to induce an effective interferon.

The present invention is directed to obtaining MIT protein type substance by removing toxic matters to eliminate the conventional drawbacks as described above and to provide an innoxious intereferon-inducing substance, inducing agent and process for producing them. The inducing substance can be extracted in large quantities not only from the human serum but also from the human urine, animals as well as vegetables, is innoxious and hence does not produce the ill effects. It is able to permeate through the cell membrane, effectively acts on the human DNA thereby to induce various interferons to correspond to a wide range of antigens, imparts effective activation to the lymphocytes and to the malnutritive cells, makes it possible to cure the predisposing cause of disease, does not produce the ill effects even when dosed continuously, has a wide range of application and can be mass-produced.

The essence of the interferon has not yet been clarified and no theoretical explanation has been given. The conjecture goes only that the interferon might be a kind of glycoproteins. With such a background, the present invention recognizes the importance of the chromoproteins and nucleoproteins as the really effective interferon-inducing substance. Thus, the present invention comtemplates the obtaining of an innoxious interferon-inducing substance which has a strong and wide immunity effect but does not cause ill effects, and which can be produced on a mass basis by removing heteroenzymic proteins and proteins of a hetero-arrangement from those mentioned above by means of a specific oil bath, sufficing the necessary proteins for the organs with the glycoproteins, nucleoproteins, chromoproteins and phosphoroproteins equivalent to the human blood and removing only the toxic proteins without decomposing the proteins of normal arrangement.

According to medical science at present, pathogenic germs are believed to be antigens of various kinds and types each having a peculiar condition of each disease. However, I have conceived that the real cause of diseases results from the blocking action of the heteroenzymic proteins and proteins of the hetero-arrangement formed by genes of various kinds and types that the pathogenic proteins possess. As a result of intensive studies for years, it has now been found that the essential amino acids for forming the immune bodies (conjugated proteins to form the antibody for the mating antigen) and detoxicating conjugated proteins are consumed and become insufficient in order to detoxicate the above-mentioned toxic proteins and cancerogenic substances such as tar and since these essential amino acids are not produced in the human body, this deficiency leads to the loss of functions of the cells of organs and to the deficiency diseases of the essential amino acids such as carcinoma and other inflammatory diseases.

Based upon this finding, the present invention develops a novel substance which can become an innoxious interferon-inducing substance and can be used as the material for the synthesis of necessary proteins of various kinds and types by selecting the kind of the essential amino acids to be sufficed by the information of the messenger RNA (ribonucleic acid). By supplementing the interferon-inducing element to fill up the essential amino acids whose principal problem has been their incapability of autoproduction, the original functions can be recovered and mal-nutrition can be improved. Thus, the present invention provides an innoxious interferon-inducing substance which is entirely novel, has carcinostatic action, contains none of the heteroenzymic proteins, proteins of the hetero-arrangement and cancerogenic tar components, can permeate through the cell membrane and can be extracted from various raw materials other than human serum.

The interferon-inducing substances containing the heteroenzymic proteins or proteins of the hetero-arrangement consume the precious amino acids and invites the deficiency of the essential amino acids, thereby accelerating the disease and the side action whereas those containing the cancerogenic components can not be permitted as medicaments because the tar components are regarded as the cancerogenic substance. In order for the inducing substance to be really effective and innoxious, these heteroenzymic proteins, proteins of the hetero-arrangement as well as the cancerogenic tar components shoudl be removed. Only when these detrimental components are removed, can the inducing substance permeate through the cell membrane and effectively act upon the human body.

Examples of the substance of the present invention are as follows.

The substance of the invention can be obtained from such raw materials as the serum, urine, the whole animal individuals including fish and shells and vegetables such as soybean or the like that contain all kinds of the essential amino acids, by decomposing and removing the heteroenzymic proteins and proteins of the heteroarrangement that are unavoidably contained in the starting proteins and are formed by genes having a strong blocking property, but not decomposing the normal protein, and by collecting the residual normal proteins. In order to remove the harmful and detrimental components by decomposition while leaving the normal proteins, even a slight temperature error can not be accepted. According to the conventional method, however, it has been extremely difficult to carry out the heat-separation at a high level of accuracy and it has therefore been impossible to remove only the poisonous and detrimental components without decomposing the normal proteins.

In a distillation still used conventionally, for example, a part of the starting proteins is dehydrated, solidified and carbonized onto the wall of the still even if with stirring, whereby the thermal conductivity lowers to a marked extent and a temperature difference as large as 200° C. occurs between the raw material near the still wall and the raw material at the center or between the surface and inside of the protein mass. Thus, it has been quite impossible to uniformly control the heating. In such a case, tryptophane is converted to tar and tyrosine is tyraminated, for example, while tyrosine is decarbonized due to the high heat. As a consequence, the decomposition loss of the effective proteins is too great for the substance to be used as a practical medicament.

To remove this problem, the present invention carries out oil bath heating wherein the fine granular raw material is put into oil placed in a heating pan and the oil is heated so as to uniformly heat the raw material. In this manner, it becomes possible to perform the heat-separation in a stable manner at a high level of accuracy. Thus, it becomes possible to separate and remove the heteroenzymic proteins and proteins of the hetero-arrangement from the polypeptide bound portion, to perfectly eliminate the occurrence of the cancerogenic tar and to obtain a highly effective, innoxious interferon-inducing substance while minimizing the decomposition of the effective proteins of normal arrangement.

The residual MIT isolated as the result of the above-mentioned oil bath heating is adsorbed onto carbon of a carbonized product or onto active carbon. After water is added to the proteins adsorbed, they are boiled. After cooling, the fat component and the protein components dissolved in the water that are separated into two layers are fractioned using a separating funnel to remove the former. The carbon is removed by filtration and the filtrate is then concentrated by drying. Soluble components are then removed by the addition thereto of acetone, thereby providing MIT containing several innoxious conjugated proteins (glyco-, nucleo-, chromo- and phosphoro-) which is equipped with, the essential amino acids of the levo-rotatory α-order. (If cancerogenic tar is formed when the heating is made to a temperature higher than 298° C. during the heating step, the resulting tar component is removed by dissolving the MIT in a protein-insoluble solvent such as benzene or hexane.) Alternatively, after the resulting MIT is dissolved in water, boiled and weighed to determine the power factor, it may be adsorbed onto grape sugar powder, starch powder, active carbon powder or acid clay powder and then dried to yield the MIT adsorbed onto the active carbon powder, the acid clay powder, the grape sugar powder or the starch powder. Still alternatively, it is possible to obtain innoxious interferon-inducing substances as the detoxicated novel substances such as MIT amino acids derived from the above-mentioned MIT, MIT amino acid esters and mixtures of the MIT amino acid esters obtained by leaving fats and fatty acid esters containing sugar.

The innoxious interferon-inducing substance is a substance having the action as described below. Namely, upon invasion of pathogenic germs and cancerogenic substances, large quantities of the precious essential amino acids, which are not auto-produced in the human body, are consumed for the formation of the immune bodies (proteins to form the antibody to cope with the antigens) and of the detoxicating conjugated proteins so that the essential amino acids ensure the normal functions of cells of organs become insufficient, thereby leading to the formation of the cancer tissues exhibiting the inflammatory diseases due to mal-nutrition. The novel substances of the invention are equipped with, essential amino acids which provide sufficient amounts of the interferon proteins having various kinds of amino acid arrangements to correspond to the nucleotide arrangement of the messenger RNA as the synthesizing materials to be synthesized by the memory synthesis mechanism of twenty kinds of amino acids of three each nucleotides. The substance has such actions as the recovery of the production of immune bodies, blood, complement, hormone, cell membrane, stromas, nucelic acids and reticular tissues lowered due to the deficiency of the amino acids that can not be autoproduced in the human body. It permeate through the membrane because it is innoxious, suffices the cell with nutrients and is helpful as the protein material to be synthesized by the instruction of the DNA.

[I] The study of cancer is time-honored. Records are aviable from the days of Hypocrite. Though various theories have since been established, such as the black bile theory according to the liquid pathology, and the lymph coagulation theory, no definite progress has been made in clarifying the condition of the disease, its therapy and medicaments. The carcinoma is a tumor from the epithelial cells while the sarcoma is a tumor from the nonepithelical cells, but both constitute mal-nutrition of the cells. In 19th century, Hilhillo developed the fundamental theory of cell pathology and asserted in 1855 that cancer cells are not produced afresh in the human body but the cancer is the purest disease of the cells per se. This pathological conception laid the foundations of modern medical science.

[II] Recent studies of the interferon-inducing substances has clarified the presence of such substances in the serum. Though the substance is not yet put to practical use as it is present in only a trace amount, it is known as the substance that rejuvenates the lymphocyte and macrophage and secretes proteins having suger chains into the body juice upon invasion of the virus, whereby the cells coming into contact with the interferon comes within a few hours into the antiviral state that does not allow the growth of the virus. Amongst others, the interferon is known as the substance having the anti-virus action and proliferation and checking the growth of the tumor cells but not exerting the blocking action to the sound cells. Though attention has so far been attracted only to the glycoproteins, I believe that the nucleoproteins, chromoproteins and phosphoroproteins are no less important than the glycoproteins and hence, have made researches for a substance which is innoxious and nutritious to the cells and is capable of permeating through the cell membrane. The present invention is completed on the basis of this conception.

[III] Natural proteins are optically levo-rotatory and nutritious proteins are limited to those of the α-order. The body portions, hairs, vessels, organs, muscular nerves, bone-marrow, cartilage and the like of the human body all consist of cells. The cells in turn consist of various proteins, and nucleic acids consist of bases of amino acids. Various pathogenic viruses, snake venom, mold venom and so forth are nothing but the inhibition of proteins containing proteins of the hetero-arrangement and heteroenzymic proteins. The number of kinds of proteins is indefinite, but they are synthesized by the genes of nucleic acids depending on the combination and arrangement of only ten each kinds of essential amino acids (among which two are peculiar to children and eight to adults) and general amino acids.

It is an extremely important fact that vegetables autoproduce partially the essential amino acids whereas animals never auto-produce them in the body. This is the very cause of cancer. Hence, animals can not maintain their lives unless they take the essential amino acids from the outside, or, from weak animals, insects and vegetables as food.

On the other hand, the general amino acids are auto-produced in the body in conjunction with the essential amino acids. It goes without saying, therefore, that the quantity of the interferon-inducing substance of the MIT amino acids retained in the body plays the decisive role for life. The hemoglobin of the animal blood functions in vivo in the same way as that of the human blood. It is a known fact, however, that the human being is killed instantly upon being transfused with animal blood because the hetero-enzymic proteins and proteins of the hetero-arrangements synthesized by the genes formed in conformity with the environment for a myriad of years are mixed in the proteins consisting of the essential amino acids and amino acids of the normal arrangements that are taken into the blood from the outside.

In rare cases, the amino acids of the hetero-arrangements are formed also in the human body by malignant genes. This is known as one of hereditary diseases. The amino acids of the hetero-arrangement are bound to the stroma of the hemoglobin proteins in place of the amino acids of normal arrangement, thereby causing the malignant hemolytic anemia. The proteins of the hetero-arrangement are called labile hemoglobin and it is known that their bonding to the stroma is extremely weak. If left as such, the patiens of the blood containing the proteins of the hetero-arrangement would die and it is an incurable disease at present for which the only remedy is to replace the whole blood of the patient by normal blood.

At the time of illness, the consumption of the essential amino acids that are not auto-producible becomes greater than the intake whereby they become insufficient and worsen the case. In such a case, if the MIT of the present invention equipped with, the detoxicated MIT amino acids and consisting of 20 kinds of amino acids, or the derivatives of the MIT, are taken, they provide the following effects. Since they are innoxious and can permeate through the cell membrane, they cure the patient of the hypoproteinamia such as of kidney disease and cure uremic hepatitis and clean the blood of the patient whose capacity to take the essential amino acids is lowered and whose detoxicating action in the kidney decreases, without resorting to the artificial kidney or the blood filtration without consuming in the liver and kidney the large amounts of the precious inducing substances in order to detoxicate and discharge the heteroenzymic proteins and proteins of the hetero-arrangement contained in the proteins taken as food.

The MIT amino acids are the vital factor which permit the functions of respective organs and are the basis of cell nutrition. The effect brought forth by removing the toxic proteins contained in the proteins is observed more remarkably in the ill or the aged having reduced immunizing power as compared to the healthy who have the innoxious essential amino acids in their bodies and high immunizing power. Since the MIT amino acids which function as the immunity-inducing substance and do not need the further consumption of the essential amino acids are supplied to the patient, whose resistance has been reduced, as the essential amino acids are consumed, and become insufficient for detoxicating the germs in the air or the toxic proteins contained in the food, they increase the immunity power and have vital significance.

The proteins are broadly classified into the simple proteins and conjugated proteins (glyco-, nucleo-, chromo- and phosphoro-proteins). The former is hydrolyzed into the amino acids and only maintains the nutrition of the body. Hence, it is not possible to remedy the disease by taking only the amino acids. The proteins having an especially close relationship with diseases are the nucleo-proteins as one of the conjugated proteins which are bound to the simple proteins and the glycoproteins that are the prosthetic group to the nucleoproteins and have the saccharide structures such as galactose, mannose, fucose and the like. Of the utmost importance among them are the chromoproteins having the biochemically important functions. This group includes hemoglobin, myoglobin, cytochrome causing the oxidation-reduction in vivo, catalase functioning as the catalyst for the decomposition of hydrogen peroxide and peroxidase. All of the hyaloproteins of the ligament and vitreous body, the chondromucoid of the ointment, the hyaloproteins of the lower glands of the jaws, the blood sugar, the heparin for the blood coagulation of the liver and heart and other glycoproteins and chromoproteins for forming the cell membrane are synthesized in vivo by the innoxious amino acids. The number of kinds is extremely large and all the solid portions of the human cells contain the proteins as important constituents. The nuclei of the cells of organs combine with the pigments and nuclei of 20 kinds of amino acids, with sugar and phosphorous to form the necessary proteins performing the necessary functions provided that they are perfectly equipped with the necessary components.

In other words, the following have been clarified. Namely, DNA is not associated only with the heredity. Of the DNA and RNA having the same nucleotide arrangement, the information (nucleotide arrangement) contained in the DNA chain is as such received by the RNA, which is called the messenger RNA, and then combines with the ribosome granules. Further, various groups of three each nucleotides forming the proteins having the amino acid arrangements to correspond to the nucleotide arrangement of the messenger RNA are memorized as the code indicative of the 20 kinds of amino acids. Furthermore, the cells synthesize the proteins from the innoxious essential amino acids so as to be suitable for the functions of the respective organs. To perform its function, on the other hand, the RNA calls for the supplement of those materials which cope with the antigens as the proteins of the hetero-arrangement and hetero-enzymic proteins formed by the genes such as virus, as exemplified by amino acid glycine, cystine, methionine and tryptophane, instructs the immune proteins to fit to the antigens of various kinds and types and thus forms the antibodies.

As to the occurrence of diseases, it is most reasonable to believe that the patient can not cope with the active growth of the antigenic virus and consumes the essential amino acids along with the increase in the formation of the antibody whereby the essential amino acids become insufficient as they are not auto-producible in vivo, thus losing the function allotted to each tissue and resulting in the disease. Though the allergy theory is commonly accepted at present, it is an irrational theory. According to this theory, the antibody does not exhibit the defense reflex and so long as the formation quantity of the antibody is small, it prevents the occurrence of diseases but when the antibody to cope with the antigen increases, there occurs the hypersensitive reaction which eventually results in the diseases. However, the cause of the occurrence of the diseases can be explained more clearly by assuming that since the essential amino acids as the materials for the immune body are not auto-producible, the interferon-inducing substances become insufficient with the increasing amount of the antibody whereby the production of the interferon as the immune body becomes impossible and the deficiency of the essential amino acids causes the nutritive defects of the tissue cells and deprive them of their normal functions.

As the cell nutrition drops markedly and cells of lower proteins cause inflammation and infiltration. At the same time, weak cells grow in vain while losing their functions. Thus, wastes and consumption of the precious proteins such as the conjugated proteins to form nuclei, the glycoproteins to form the cell membrane and the stroma and the chromoproteins to form the blood accelerate the deficiency of the essential amino acids that are not auto-producible, until at last malnutrition extends over the whole body and possibly results in such incurable diseases as cancer. Hence, the nucleoproteins and the chromoproteins are more important than the glycoproteins.

Whipple developed a protein equilibrium theory holding that the total amounts of the proteins in the blood and organs maintain a predetermined mechanical equilibrium with the total amounts of the proteins in the tissues. This clearly explains that when the proteins in the blood and organs are consumed, they are carried from the tissue of each portion of the body through the vessel, thereby lowering the nutrition of the tissues as a whole. This theory explains clearly the real cause of the metastasis of the cancer.

The inflammation of the cell is caused when the cell loses its function due to the nutritive defects, damages and radioactive rays, that is to say, due to the deterioration of the overall life conditions. When the pneumocaccus floating in the air is incubated, is irradiated with ultraviolet rays near 2537 Å for 20 seconds at a distance of 30 cm using a 30 W UN sterilization lamp and then inspected with an electron microscope, the baccilus first swells twice, has a shadow and is cubic. Secondarily, it comes to possess the shadow around it and as the cell membrane collapses and the proteplasmic protein leaks out of the membrane to cause the infiltration and thus becomes errosive. Thirdly, it does not form the shadow in the same way as cancer and is observed to have changed to the pavement cell in which bacilli pile one upon another. Thus, the bacillus is found to be equivalent to the cell of the cancer in which only the nuclus is left. Thus, it is recognized, as asserted by Hilhillo, that cancer is purely a disease of the cell.

[IV] The innoxious essential proteins and their derivatives function inside the body as the interferon-inducing substances. Though their amino acid contents vary depending upon the raw materials employed, they are all equipped with, the essential amino acids. They remove the heteroenzymic proteins and proteins of the hetero-arrangement and eliminates their blocking property. They do not form the tar components, the cancerogenic substance formed due to the non-uniform heating in the conventional distillation still or the like, but consist of the conjugated proteins bound with a part of the 20 kinds of amino acids. They are helpful, as the raw materials, for forming in vivo various hormones, interferons as the immune bodies of various kinds and types, the blood and other essential vital factors. Hence, the heretofore known glycoproteins alone are not the interferon-inducing substance.

All of the carbon-adsorption component and acid clay-adsorption component of MIT and the grape sugar component obtained by dissolving the MIT in acetone are suited for peroral administration. The aqueous or physiological saline solution of the MIT, the aqueous MIT amino acid solution formed by acid hydrolysis of the MIT and the grape sugar component obtained by removing the soluble components by acetone may be used for subcutaneous injection after sealing the solution in an ampule and dissolving it in distilled water at the time of use. If inorganic components are added through the food to the mixed component of the fatty acid ester and the sugar, there is provided an almost perfect nutrient. All of them are dark brown powder but the carbon-adsorption component is black. The mixed component of the innoxious essential amino acids, fatty acid esters and saccharides (mono-, di- and hexa-) formed by acid hydrolysis of free hydrocarbons is yellowish brown and has high efficacy. When heating is effected at a temperature higher than 298° C., there is formed a tar component. The mixed component obtained by dissolving the tar component in benzene or hexane to remove it has a grey color, but since the effective hydrocarbons are lowered, the component has only limited efficacy.

The MIT and the MIT amino acids are strongly hygroscopic are easily susceptible to oxidation and can be easily decomposed by hydrogen peroxide. They are decarbonized upon being directly irradiated with sun light. When an alkali is added dropwise to the aqueous solutions of the proteins and amino acids, the proteins are separated from the conjugated protein and precipitate the simple proteins as white powder while the amino acids are also decomposed into simple protein amino acids and markedly lose the nutrient values for the body.

In the examples of the present invention, these components are converted into the carbon-adsorption component and the acid clay-adsorption component in order to prevent their hygroscopicity. The MIT component, the saccharide component treated with acetone, the starch component and the MIT amino acid component are stored as they are sealed in ampules. However, the ester component is less hygroscopic. The ester component is decomposed into 20 kinds of conjugated bound amino acids by the phosphatase and sulphatase in the body and are employed as the material for the protein synthesis.

Among those obtained from the vegetables proteins, only the one obtained from soybean is perfectly equipped with the essential amino acids in the same way as the animal proteins. However, most of those which are obtained from other vegetables and germs partially lack the essential amino acids.

It is also possible to obtain the innoxious interferon-inducing substance from the antibody of the blood and urine in accordance with the process of the present invention.

When blood is used as the raw material, the production process comprises first dehydration-drying the blood, solidfying it, pulverizing it into fine powder, then adding an oil to the powder, and performing the oil bath heating in the same way as mentioned above, thereby yielding the innoxious interferon-inducing substance in the same way as when the animals or vegetables are employed as the starting material.

Next, the explanation will be made about the case where urine is used as the raw material. The urine components include the antibody proteins that are conjugated with the hippuric acid, uric acid, ammonia sulfate, sodium chloride and sodium sulfate, and these antibody proteins contain the inducing substance of the essential amino acids.

The inducing substance is obtained in the following manner. The solid content obtained by drying the urine is first heated to 203° C., for example, whereby the hippuric acid, uric acid and ammonia sulfate are decomposed and evaporated, thereby leaving a trace amount of a salt content. The antigen in the anitbody is decomposed by the heat of treatment and the heat-resistant protein consisting of the amino acids remains. The residual components are eluted with water and after the evaporation drying, soluble components are removed with acetone, and the residual matter is dissolved in water to yield the MIT.

In this manner, the urine can be used as the starting material besides the blood so that hospitals can easily secure the effective raw materials in large quantities by making use of the urine of patients.

As already described, animals and vegetables can be used as raw materials. In this aspect, too, it is possible to secure large quantities of the raw materials. Of the animals, the snails, for example, are extremely excellent raw materials. African snails are present in such large quantities they can hardly be exterminated.

Natural amino acids consist of amino acids that are optically levo-rotatory and have an $NH_2$ group at the α-order. The MIT and MIT amino acids are soluble in water and acid but their esters are soluble in acids but not in water. They are difficultly soluble in alcohols and insoluble in benzene, chloroform, benzene, hexane, acetone and ether.

The MIT and its dervatives supply nutrition to a serious case whose resistance has been reduced, without producing any ill effects and increasing the immunizing power. As they easily permeate through the cell membrane having the permeation resistance to detrimental matters, the development of these novel inducing substances of the present invention makes it possible to perfectly induce the effective interferon in the cancer resulting from mal-nutrition of the cell and to cure the inflammation and tumors throughout the bodies in a relatively easy manner. For this reason, it is no exaggeration to say that these substances are predisposing anti-tumor substances.

That is to say, the substance of the present invention is equipped with the necessary kinds of the essential amino acids or is perfectly equipped with the whole kinds of the essential amino acids, induces and supplements the synthetsizing materials without causing deficiency for the protein synthesis mechanism in vivo and prevents the occurrence of the disease. Further, it suffices the ill cells with the nutrients, improves the inflammation, activates the cells, permits the tissue cells to perform their inherent functions, promotes the blood, hormone, cell membrane, stroma, nucleic acids immune bodies as well as the reticular cells and allows sound metabolis and normal life function. Thus, the substance of the present invention is a novel inducing substance which is effective for curing disease resulting from essential amino acid deficiency.

Most of medicaments of foreign make available at present pursue the purified crystal and could cause possible allergic defects or functional defects of the liver. These protein type medicaments neglect the mixture of the heteroenzymic proteins and proteins of the hetero-arrangement and hence, it is quite natural that the toxicity of the medicaments should become a serious social problem.

[V] It is cytochrome that plays the leading part in the oxidation-reduction of the living body and heme proteins are those consisting of hemin compounds bound to a part of the peptide chain. Its skeletal structure and the position occupied by the heme have also been determined by X-ray diffraction of the heme proteins analogous to the heme enzyme. The structural information about other enzymic proteins will be obtained gradually in the future.

It has been found that like the heteroenzymic protein, the proteins of hetero-arrangement have the heme structure in which the heme chain has a normally wound helical form and is bent into a skeltal structure of spherical form or the form of ellipsoid of revolution, and it has also been found by means of analysis of the chemical kinetics that there is a difference of the binding power at the bound portions between the stroma and the enzymic proteins. Heating with precision control unbinds the bound portions and causes the denaturation of the hetero-enzymic proteins and proteins of the hetero-arrangement without changing the peptide chains normal arrangement whereby the peptide chain of the former gets loose and stretched and the peculiar cubic arrangement of the bound portions between the stroma and the amino acids of the proteins of the hetero-arrangement and hetero-enzymic proteins is lost, thus leading to the loss of activity in the case of the enzyme.

Reports have been filed, however, that among the commercially available protein type drugs, some still exhibit activity even after the application of hydrolytic heat at 100° C. and the subsequent repetition of purification by means of recrystallization, while others producing ill effects have a decomposition point of 203° C. In order to permanently terminate the activity of the hetero-enzyme, to extinguish the toxicity of the proteins of the hereto-arrangement and to obtain 20 kinds of amino acids required for surpressing the cancer, the present invention applies uniform heat to the raw material so that the peptide bound portions of the hetero-enzymic proteins and proteins of the hetero-arrangement are uniformly heated by the oil bath heating at a temperature of 203° C. or more with accuracy and the bound portions of the peptide chain are denatured thereby splitting and breaking the chain.

Since the peptide chain of normal arrangement is not broken, it is possible in the present invention to carry out the oil bath heating in the room without requiring a device for removing offensive odor and a device for heating and stirring unlike the conventional heat-separation method which involves the formation of large quantities of ammonia, hydrogen sulfide, carbon monoxide, tar, amine and the like due to the proteolysis. The fat bound to the glycoproteins is protected by the cell membrane and the glycoproteins, which can be obtained only in a limited quantity in the case of the hydrolyzing method, can be separated to increase the yield together with the free fats that are isolated immediately before the carbonization of the cell membrane. Thus, the process of the invention is characterized in that the separation is effected by uniform heating of the granular raw proteins by means of oil bath heating at a temperature not lower than 203° C. It is also possible to carry out the dry-heating by adding a suitable amount of edible oil to the raw material.

On the other hand, the decomposition points of amino acids are tabulated in Table 1.

As described above, the process of the present invention obtains the innoxious interferon-inducing substance by means of bath oil heating. However, the lower the heating temperature, the greater the kinds of the essential amino acids of the conjugated proteins that are bound to the amino acids, and the higher the heating temperature, the smaller the number of the essential amino acids and the narrower the range of immunity.

TABLE 1

(tabulated in accordance with decomposition point)

| | Name | Decomposition point (°C.) | o essential amino acids Δ essential amino acids for children |
|---|---|---|---|
| $A_o$ | valin | 315 | o |
| | norleuicine | 301 | o |
| | tryptophane | 298 | o |
| A | alanin | 297 | o |
| | leuzin | 293 | o |
| | tyrosine | 290 | |
| B | phenylalanin | 283 | o |
| | isoleucine | 280 | o |
| | methionine | 280 | o |
| | aspartic acid | 271 | |
| | oxyproline | 270 | |
| C | cystine | 258 | o |
| | threonine | 251 | |
| D | cystein | 240 | |
| | thyroxine | 232 | |
| | glycin | 232 | |
| | theeline | 228 | |
| | lysin | 224 | o |
| | proline | 220 | |
| E | arginin | 207 | Δ |
| | glutamic acid | 206 | |
| F | histidin | 155 | Δ |
| | ornithine | 140 | |

In order to destroy and remove the heteroenzymic proteins and the proteins of the hetero-arrangement, it is necessary to carry out the heating at a temperature of at least 203° C. with a high level of accuracy. On the other hand, by suitably selecting the upper limit for the heating temperature, it becomes possible to select the amino acids of the kinds corresponding to the decomposition points, as exemplified below.

| Heating temperature | Groups classified temperature-wise |
|---|---|
| 203° C.–297° C. | Ao |
| 203° C.–289° C. | Ao, A |
| 203° C.–269° C. | Ao, A, B |
| 203° C.–250° C. | Ao, A, B, C |
| 203° C.–219° C. | Ao, A, B, C, D |
| (to cover all of the eight kinds of the essential amino acids for the adult) | |
| 203° C.–205° C. | Ao, A, B, C, D, E |

If the component using the material principally of the innoxious essential protein type equipped with the eight kinds of the essential amino acids included in Ao, A, B, C and D is dosed to the adult, the range of the immunization effect of the interferon is extremely wide. However, those components which lack parts of the eight kinds, e.g., those only of Ao, only Ao and A and only A and B and the like have a reduced number of inducing substances in comparison with the component equipped perfectly with the eight kinds and their immunizing range is also reduced. Depending on the factors remaining in the body, however, such components still exhibit some effects for specific diseases. For example, valin is useful for the recovery of muscular fatigue, tryptophane for detoxication, conjugation and the hemoglobin-increasing action (in cooperation with prolin and oxyprolin) and methionine is helpful for producing the immune body.

In comparison with the heretofore known substances, the innoxious interferon-inducing substance in accordance with the present invention has a revolutionary antitumor action. Since the substance of the invention can permeate through the cell membrane and is innoxious, detoxication and excretion are not required in the liver and kidney. In other words, the substance does not waste the precious inducing substances retained in the body. The antitumor action of the substance starts instantaneously or within a short period after dose such as within one day, and the inducing substance gathers at the focus of the disease. It has been found that the patient himself could detect the location of the focus through the temperature sense (due to the cell activation) and the portion at which the temperature sense was detected could always be improved.

The inducing substance acts on the DNA whereby the protolysis is carried out and the immune protein, i.e., the interferon, is produced. However, it is believed that the combination of the inducing substances varies with the antigen and the interferon is not a single kind but is extremely versatile. The selective combinations are made out of the twenty kinds of amino acids. Especially, the patient uses the conjugated body of the MIT amino acids that are difficultly auto-producible as the basis of the combinations, and if the combination is perfectly equipped with the necessary components, the perfect interferons having all kinds of immunity are produced in accordance with the antigens. As the substance of the invention has a wide range of the antitumor action and is able to contain the chromoproteins that the conventional substances lack, the present substance is effective for the myeloma which is difficult to cure at present as well as for diseases at various portions of the human body.

[VI] Kennaway et al reported that the hydrocarbons of the fibrins and the like are polymerized by dry heat to form polynuclear aromatic hydrocarbons (cancerogenic tar) and they regarded them as the cancerogenic substances. It has since been found that the important elements such as tyrosine among the amino acids forming them are principally decarbonized at a temperature higher than 290° C. and are converted to the toxic tyramine while more than 70% of tryptophane is also converted to tar at a temperature higher than 298° C. It has also been found that since the conventional heating method fails to uniformly heat with a high level of accuracy, the temperature partially exceeds 298° C., thereby forming tar.

The polynuclear aromatic hydrocarbons such as benzpyrene are colorless crystals and volatile. They have a boiling point of 342° C. and are soluble in water. The baked product commercially available at present has a boiling point of 342° C. and are believed to contain cancerogneic tar. Unless the tar is removed, there can not be an innoxious medicament for the human body. Hence, they are not permitted as the pharmaceutical and can not be used.

In the present invention, the heating method is improved by way of the oil bath heating so as not to form the tar and it becomes possible to provide uniform temperature control with a high level of accuracy by placing the granular raw material in the oil and heating it. By the use of a temperature not higher than 298° C., the formation of the tar can be perfectly prevented, thereby yielding the innoxious and safe component.

Due to the decomposition of the proteins, offensive odors peculiar to ammonia, hydrogen sulfide, amine and the like are apt to be generated. In the present invention, however, the decomposition quantity of the normal proteins is so small that the formation of the offensive odor is small along without the formation of tar.

[VII] The enzymes exhibiting the catalytic action are important factors that cause the vital phenomena in vivo and are present in the saliva, gastric juice, juice of the small intestine, cerebrospinal juice and the like. The number of enzymes present in each organ and those of animals are indefinite. The human enzymes are useful for the human being. In the proteins of the animals and vegetables, however, there are those enzymes which exhibit the blocking actions of various kinds and types to the human being such as the cynamic acid poison, hydroxylamine poison, carbon monoxide poison, maloic acid poison, oxidation poison, narcotic poison and heavy metal poison. The catalase of the horse, for example, combine with the heme while the carbonic anhydrase of the animals combine with Zn of the functional group, thereby exhibiting the blocking action. Among the cancerogenic drugs put on sale on the market, some contain the heteroenzymes and their possible blocking action is a cause for fear. There is concern that they will produce ill effects in future.

The present invention provides the only method which removes the toxic proteins of the heteroenzymic proteins and proteins of the hetero-arrangement at the present moment. Fortunately, the heteroenzymic proteins and proteins of the hetero-arrangement have more unstable and weaker stroma bonds than the proteins of normal arrangement. Hence, these stroma bonds are denatured and destroyed by means of uniform heating with the oil bath, thereby removing the toxic proteins. The formation of tar on the still wall due to the direct heating is also eliminated in the present invention. These are the essential features of the production process of the present invention. It is fortunate that the toxicity is eliminated for the first time in accordance with the present invention.

The interferon-inducing substance in accordance with the present invention has succeeded in acquiring the following advantages for the first time and provides extremely remarkable effects.

(1) Capability to permeate through the cell membrane

The invention realizes for the first time the interferon-inducing substance by detoxifying the substance. The substance supplies the essential amino acids to the cells, induces and synthesizes the immunizing factor (interferon) and makes it possible to make the predisposing remedy.

As a result of intensive studies for years, the inventor of the present invention has confirmed that the disease such as the cancer is caused due to deficiency of the essential amino acids in the cells. Since the conventional interferon-inducing drugs contain the heteroenzymic proteins, proteins of the hetero-arrangement, the cancerogenic tar and the like, they can not permeate through the cell membrane and can not be supplied into the cells. Hence, it has not been possible to make the predisposing remedy.

(2) No ill effect even after continuous dose

The substance of the present invention is detoxified. Hence, it does not invite the consumption of the essential amino acids in the cells and rather permeates through the cell membrane, thereby supplying the nutrition. Not only does the continuous dose of the substance produces no ill effects but also its continuous dose positively promotes and accelerates the remedial effects. The substance of the invention enters the human cells and acts on the chrosomes thereby to induce the interferon. It is therefore different remarkably from those which rely upon the coliform bacillius for their action, for example, and is innoxious to the human being. The conventional substance can not be supplied into the cells (because of its toxicity) so that the essential amino acids are consumed due to the disease and becomes insufficient. Further, the continuous dose of the substance invites the remarkable consumption of the essential amino acids for the detoxication of their toxicity, thus leading to the deficiency of the essential amino acids and eventually producing the ill effects.

(3) It can be produced on a mass basis

As the raw material for the substance of the invention, any materials can be used so long as they contain large amounts of the essential amino acids. Hence, it is possible to employ such materials as fish, African snails (especially excellent material and present in such a large quantity as to be hardly exterminated), soybean and the urine of human being that are all readily available in great quantities.

(4) Wide application range—containing various conjugated proteins

The substance of the invention has remarkably excellent effects for diseases such as cancer as described above. A number of clinical cases evidence the efficacy of the present substance.

[VIII] In order to obtain the interferon-inducing substance having the antitumor action, it is a limiting condition that the raw material used be equipped with, or perfectly equipped with, the essential amino acids. Among the protein type drugs directed to obtain the symptomatic effect, many produce allergic disease and the defects of the liver function as ill effects. The heteroenzymic proteins and proteins of the hetero-arrangement admix with the normal proteins, continue to remain even after the repetition of the purification-recrystallization, exhibits blocking action and are thus the real cause for the ill effects. In accordance with the removing method of the toxic proteins of the present invention, it becomes possible to remove the substances causing the ill effects even when those raw materials are employed as the materials for the proteins which are not directed to obtain the antitumor substances, such as the whole or a part of the individual having the proteins of the living portion of the living things, e.g. animals and vegetables containing mold, ground germs and pathogenic germs.

Next, the present invention will be explained in further detail with reference to embodiments thereof. 700 g of a living sea bream equipped perfectly with the essential amino acids and 300 g of the dried snail meat are used as the raw material. To 1 kg of the raw material is added 1,000 cc of water. The material is then boiled. The bones and shells are selectively removed. The residue is then sliced with the boiling water and pulverized by an electric mixer. The pulverizate is placed in a porcelain pan, heated and then evaporated to dryness. The fine granular material is put into 100 cc of the soybean oil in a porcelain pan and heated. The oil temperature is controlled so as to keep the temperature of the material at 204° C.±1° C. From the start of the heating, the material becomes dark brown around 180° C. and the glycoproteins combined with the fat and protected by the cell membrane are isolated together with the fat prior to the carbonization of the cell membrane. When the fat is heated to 203° C. or more, the raw proteins admixed in the fat are carbonized and become black particles due to the uniform heating by the oil bath. The heteroenzymic proteins and the proteins of the hetero-arrangement are isolated from the polypeptide chain of the proteins as the bound portions are denatured, and are broken, evaporated and removed. However, the proteins of normal arrangement are not decomposed. No poisonous gas due to the decomposition such as ammonia, hydrogen sulfide, carbon monoxide, amine and the like occurs and the air contamination is as low as that in frying the dishes in the daily kitchen. No stirrer is required. When the heating is stopped after maintaining the temperature at 204° C.±1° C. for about 3 minutes, only the heteroenzymic proteins and proteins of the hetero-arrangement are removed. In the conventional method not using the oil bath heating of the present invention, the proteins as the raw material exhibit the characterizing feature in that they become a viscous mass, adhere and solidify onto the still wall, thus hindering the heating of the contents. Consequently, there occurs a temperature difference of as great as 150°–300° C. between the solidified matter on the wall and the contents. Even when the agitation is made to heat the content to a desired temperature, the proteins near the wall are always decomposed to form tar and are converted to the tar.

By contrast, in the present invention, the whole raw material is heated while the temperature is uniformly controlled with a high level of accuracy and the invention has succeeded in decomposing and removing only the heteroenzymic proteins and the proteins of the hetero-arrangement.

The resulting carbon-adsorbed protein component is collected hot and is then pressed by a pressure juicer to remove the oil. Further, 1000 cc of the water is added to the carbon-adsorption content and boiled whereby the fat content as the upper layer after cooling is fractioned using a separation funnel. The excessive oil content is removed and the residual carbon-adsorption content and proteins are further boiled and dried, thereby yielding a dark brown solid matter. Using this solid matter, granules for the glucose injection can be prepared in the following manner. Acetone and glucose are added to the solid matter and are sufficiently shaken to remove the soluble components. After drying over a water bath, the resulting glucose component is milled into fine powder, which is immediately sealed into a glass ampule. At the time of use, the MIT glucose powder in the ampule is dissolved in distilled water for injection use. It is also possible to obtain 12 g of the MIT component by adding 500 cc of acetone to the above-mentioned solid matter to remove the soluble components and then pulverizing the matter obtained. Alternatively, purified active carbon or acid clay or glucose is added to 12 g of the pure MIT collected at normal temperature to a total amount of 120 g and 100 cc of the water is then added. After boiling over the water bath and the subsequent drying and pulverization provides 120 g of the active carbon-adsorption component, acid clay-adsorption component of glucose-adsorption component having a power factor of 100 mg in an amount of 120 g. Still alternatively, 118.8 g of starch is added to 1.2 g of the MIT component at normal temperature to yield 120 g of the starch component having a power factor of 10 mg, which is then sealed in a glass ampule or stored under protection against moisture. 11.5 g of the pure MIT component may be dissolved in physiological saline solution or in distilled water for injection use after determining its power factor.

The MIT amino acid component can be obtained in the following manner. 12 g of the MIT component is added to 200 cc of water and 30 cc of hydrochloric acid to effect hydrolysis over the water bath and is then filtered. The filtrate is concentration-dried over the water bath to yield 10 g of the dark brown MIT amino acid. This can be used for peroral administration. Alternatively, it may be used for injection after it is dissolved in physiological saline solution or in distilled water and its power factor is determined. Further, 10 g of this MIT component is added to 100 cc of water and 50 cc of 75% ethyl alcohol, and sulfuric acid is then added dropwise to this mixed solution so that the reaction is permitted to proceed until the dark brown precipitate is no longer formed. It is then boiled over the water bath to complete the esterification, followed by drying to yield 6.8 g of the MIT amino acid ester.

When the MIT is partially hydrolyzed, there can be obtained an MIT-derived protein such as peptide or peptone.

Incidentally, the aqueous solution component of carbon and protein separated from the fat component floating in the water in the aforementioned physical extraction step contains large quantities of hydrocarbons. To mix them as saccharides, they are first dried. 176 g of such components are then added to 500 cc of water and 35 cc of hydrochloric acid to perform the hydrolysis. The filtration is then effected to remove the carbon content and the resulting solution is concentrated whereby the hydrocarbons are converted to mono-, di- and hexa-saccharides and the residual fats and proteins are converted to fatty acids and amino acids, respectively. 70 cc of methyl alcohol is added and sulfuric acid is then added dropwise to the mixed solution till no precipitate is observed. The resulting mixture is boiled over the water bath to remove the excess acids and to complete the esterification. The product is dried to obtain 10 g of the mixed component.

The heating to a temperature higher than 298° C. in accordance with the present method and the conventional heating method involve the problem that tar is formed. It is however possible to remove free hydrocarbons (containing the tar) using benzene and thereafter to dry over the water bath the mixed components of benzene-insoluble saccharides, the innoxious essential amino acid esters and fatty acid esters, yielding 9 g of the above-mentioned mixed component after removal of the residual benzene. Hexane or benzol may also be employed for the purpose of removing the tar, but benzene is preferred because it has relatively low toxicity and can be easily removed.

To prepare the injection drug, the precipitate is formed by placing the MIT in a solvent in which it is insoluble, such as alcohol or acetone, and the resulting precipitate is dissolved in the physiological saline solution or distilled water, sterilized by boiling, sealed in an ampule, stored by freezing in a dark place and used for subcutaneous injection.

In the manner described above, the innoxious interferon-inducing substance is prepared from the MIT carbon-adsorption component, the MIT component, the MIT amino acids, the MIT amino acid esters or the MIT amino acid ester components present as a mixture with saccharides and fatty acid esters by first removing the heteroenzymic proteins and proteins of the hetero-arrangement and then preventing the formation of the cancerogenic tar by dry-heating. The inducing substance induces the interferon of the protein type materials synthesized in vivo and recovers the immunizing power and malnutrition of the cells lowered due to the deficiency of the essential amino acids. Since the MIT is the precious nutrient to the cells and can permeate through the cell membrane well, it is theoretically expected to be sufficiently helpful for the predisposing remedy of leukemia. The substance permits the sound organs and their cells to exhibit their normal function and is useful as the antitumor drug and for the remedy of leukemia.

Though the foregoing explanation principally deals with the human being by way of example, the present invention embraces within its technical scope the application of the MIT component and MIT amino acid component to the animals such as the dog, cat, cow, horse, pig and so forth.

Next, examples of the invention are given in which the component has a power factor of 10 mg. The decomposing points of the carbon-adsorption MITs used in these examples range from 203° to 220° C. and contain the amino acids of the groups Ao, A, B, C and D illustrated in Table 1.

EXAMPLE 1

It has been reported that the presence or absence of the immunity is closely related to cancer. The MIT protein type component does not produce any ill effect. Of several cases who took the interferon-inducing substance consisting of the MIT protein type component, all of them equally have the immunity to most kinds of epidemic common cold (influenza) viruses and more than 95% of the cases scored a satisfactory result. Since the heteroenzymic proteins and proteins of the hetero-arrangement producing ill effects are removed, no problems are observed even when the children take the substance in the dosage for the adult.

EXAMPLE 2

When the immunity drops, abnormality is observed in the blood picture in the blood test. A patient with muscular distrophy who took the inducing substance came to show a normal value. After the administration of the substance, this patient alone was not infected with the epidemic common cold in spite of the fact that his family were caught cold.

EXAMPLE 3

Eight successful cases are observed in perfectly curing the cutaneous erosions of the dog and cat lasting for several months by scattering only once the interferon-inducing substance of the MIT carbon-adsorption component onto the seat of the disease. This evidences efficacy of the substance of the invention to the animals. However, the toxicity inspection using the animals is meaningless for those substances which are produced by the methods other than the present method and from which the toxic proteins are not removed even if they are effective for the animals because they have toxicity to man. For, in case of animals other than man, though the heteroenzymic proteins and the proteins of the hetero-arrangement produced by the genes of the animals are advantageous and innoxious, some of them exhibit toxicity to man. Accordingly, in the present invention, the examples of the medicaments for man evidence their efficacy only when they are applied to man.

EXAMPLE 4

The remedial effect and result are explained about the case diagnosed as the cancer. In this treatment experiment, 0.7 g each of the interferon-inducing substance consisting of the MIT carbon-adsorption component are perorally administered three times a day (2.1 g in total a day) or applied (about 0.3 g each on average). In stimulating the cell and permeating through the cell membrane, the MIT protein component supplies the intercellular nutrient elements and hence, increases the inflammation. This is a phenomenon which is caused as the permeation pores of the cell membrane are expanded to feed the nutrition to the cell and when the nutrition is fed into the cell, the inflammation fades away. As the cell nutrition is sufficed by the MIT formed by the essential amino acids, the cancerous inflammation (tumor) is improved and the cell is stimulated as the sound cell. It is the seat of the disease but not the unaffected part at which this stimulating reaction occurs. This phenomenon can be used for diagnosing the patient.

The part where the stimulating reaction occurs can always be improved by the continuous dose of the interferon-inducing substance of the MIT protein type component.

EXAMPLE 5

The stimulating reaction causes pain of varying extents depending upon the sensory nerves. No pain is felt at the kidney, but the body temperature rises to 38°–40° C. with a temperature sense in the case of the respiratory defects without any feeling of the pain and decrease in appetite. However, the body temperature drops within 24 hours and returns to normal temperature whereby the slight fever that has chronically remained disappears perfectly and the inflammation (tumor) gradually gets loose with the supply of the component. The blood also is cleaned and the blood picture shows normal value. The time required for the remedy of the lung cancer is about 40–60 days on average.

EXAMPLE 6

In the case of renal insufficiency, the inducing substance recovers the excretion of urine of the tissue and cleans the contaminated blood without calling for the artificial kidney and blood filtration. The peroral administration of the interferon-inducing substance of the MIT protein component (0.57 g/dose, thrice a day) immediately exhibits its efficacy for uremia. Even the serious case is perfectly cured within about 3 months.

EXAMPLE 7

In the case of the gastric cancer, the inducing substance exhibits the stimulating action without excessive pains and directly acts on the part of the tumor. Hence, two cases are obtained where the dose of the substance for 30 days provides good results to be permissible by X-ray inspection. If the pain is unbearably strong after taking the inducing substance, there is a possibility of the combined disease with the gallstone as one such case is observed. This is solved by performing the operation to remove the gallstone.

EXAMPLE 8

A normal amount is dosed to the erosion of the scarf skin of the orifice of the uterus and at the same time, the carbon-adsorption component is sprayed using a spuit. Within 10 days of the treatment, the inflammation disappears with disappearance of the offensive feeling, and two such remarkable cases are obtained.

EXAMPLE 9

There is obtained one case of treatment where a patient whose tumor at the depth of the oviduct of uterus has been difficult to remedy is perfectly cured by the dose of the interferon-inducing substance of the MIT carbon-adsorption content within only two weeks.

EXAMPLE 10

The patient who is diagnosed as having cancer of the liver is able to detect the hard tumor by touch, and his arterial blood is also contaminated. The dose of the substance for about 40 days solves the tumor at the part of the liver without any feel of the tumor by touch and purifies the arterial blood, providing the normal blood picture.

EXAMPLE 11

In the case of skin cancer, the carbon-adsorption component is sprayed onto the erosive part and is simultaneously dosed for one week, thereby forming the new scarf skin. Thus, the difficulty curable erosion for years is perfectly cured.

As described in the foregoing, the interferon-inducing substance consisting of the MIT protein type substances provide the patient with a revolutionary increased immunizing power without producing any ill effects at all. Even when children take the substances in a dose greater than that for adults for an extended period of time of more than 6 months, they cause no abnormal effects at all. They improve the inflammation from its predisposition and cause the stimulating action in the tumor tissue showing the defect of the blood stream. Though they temporarily increase the inflammation, the supply of the MIT protein components effectively improves the tumor of the cancer (inflammation).

Here, it is worth special nothing that when the MIT contains large quantities of the hemoglobin-forming chromoproteins as the most important nutrient factors, the substance stimulates the tissue having the defect in the blood stream which stimulation has not been observed conventionally, dissolves the inflammation, improves the defects due to the constriction of the tubes, also improves the blood circulation and causes drastic detoxication in the body that has not conventionally been observed. Though the combined use of the substance with ordinary medicaments having less toxicity is acceptable, the injection with those poisonous substances which are conventionally frequently employed to mitigate the pain of cancer treatment such as narcotics should not be made.

As the substance rapidly improves the blood stream, the detoxified poison causes no problem as it is excreted out of the body when the MIT protein type substance alone is dosed, but the conjoint use with the toxic medicaments producing much ill effects should be prohibited. When the toxic substance is dosed conjointly, the poisonous matters that have been accumulated in the body of the patient are detoxified extremely rapidly so that when the detoxification quantity exceeds the lethal dose, the death due to the cardiac paralysis, for example, would occur. Hence, the conjoint use is a strict contraindication and should be restricted only to the combination with the medicaments for the symptomatic treatment having no toxicity, nutrients and antibiotics. The conjoint use of the substance of the invention with antibiotics for acute diseases, especially suppurative diseases, provides excellent effects as a result of the synergestic action of the substance, but since the substance recovers the blood circulation, the dose should be reduced to $\frac{1}{3}$ for patients with hypertension, those with headache due to increase of the blood stream and those feeling chill or ague so that the dose be preferably increased to the normal level with the improvement in the condition of the disease.

Addicts of narcotics and alcohols would have ague due to the detoxicating action of the substance. Hence, the dose should be started from a reduced level and increase gradually with the progress in the recovery under the supervision of the doctor. Among the anticancer drugs heretofore provided, there are many from which the heteroenzymes and proteins of the heteroarrangement are not removed. Accordingly, these drugs provide satisfactory results before the essential amino acids remaining in limited quantities in the body of the patient become perfectly deficient, but as soon as the amino acids become perfectly deficient, the condition of the cancer gets drastically serious, leading to unexpectedly critical condition together with their ill effects.

Though the present invention is directed to the interferon-inducing substance containing the essential amino acid type compounds as described already, the technical conception of the present invention can be adapted to the extraction of the necessary proteins from living bodies by removing the heteroenzymic proteins and proteins of the hetero-arrangement from the groups of proteins or removing the cancerogenic tar component therefrom. For example, the present invention can be applied to the removal of the toxic components in extracting natural antibiotics (such as penicillin), hormones and vitamines. This can be made in the following manner.

Namely, the raw protein consisting of the whole or a part of an individual having the living portion of an animal or vegetable containing bacteria, viruses and ground germs is pulverized whether or not the raw protein is equipped with, or perfectly equipped with, the essential amino acids. In order to obtain glycoproteins present in large quantities in the cell membrane together with the fats, a suitable amount of edible oil is added if the raw material having a small fat content is employed. Uniform heat is applied by making the oil bath heating to heat the freshly formed fats of fats and glycoproteins isolated immediately before the carbonization of the cell membrane to 204°±1° C. Alternatively, dry heat of a temperature of 203° C. or more is applied in order to only decompose the proteins of the hetero-arrangement and heteroenzymic proteins without decomposing the proteins of the normal arrangement. Due to the uniform heat by the oil bath heating, the bound portions of the heteroenzymic proteins and proteins of the hetero-arrangement having weaker bonds than the stroma bonds of amino acids having the normal arrangement of the polypeptide chain are denatured, deprived of the cubic structure and thus split off from the polypeptide chain and ruptured. Since the proteins of the normal arrangement are not decomposed, however, the formation of large quantities of the tar is eliminated, and only the heteroenzymic proteins and proteins of the hetero-arrangement exhibiting the toxicity are destroyed and removed. Thus, the formation of the polyneclear aromatic hydrocarbons (tar) due to the polymerization of hydrocarbons is eliminated by the oil bath heating. The tar and fats that are formed due to the heating at a temperature of 298° C. or more or by the conventional heating method are eluted and removed as carbides consisting principally of the tar using benzene or hexane. The resulting matter is added with the water and then boiled to remove the solvent, followed by the filtration for the purpose of removing the carbon content. Thus, there are obtained the complex protein or partial protein of the detoxified conjugated glyco- and chromo-proteins of the α-order, its carbon-adsorption component, its amino acid component obtained by the hydrolysis with an acid, its $RCOOCH_3$ or $RCOOC_2H_5$ ester component obtained by allowing the COOH group of the amino acids to react with methyl or ethyl alcohol in the mixed solution with sulfuric acid or hydrogen chloride to convert the amino acid to its alcoholic compound.

Still alternatively, an alkali is added dropwise to an aqueous solution of the complex or partial proteins of the conjugated proteins or their acid hydrolysis solution so as to precipitate or separate simple proteins and simple amino acids from the conjugated proteins.

In this manner, the method of the present invention can be used as a method of removing toxic proteins mixed in the raw proteins in order to obtain those compounds and derivatives such as conjugated proteins, their partial proteins, the innoxious simple proteins and their amino acids and amino acid esters which perfectly eliminate the allergic diseases and malfunction of the liver producing the ill effects.

In addition to the mere detoxification method mentioned above, as a substance useful for the therapy of the essential amino acid deficiency such as anticancer agent, the substance of the present invention makes it possible for the first time to provide remarkable predisposing efficacy as it contains the conjugated proteins whereas the simple proteins used conventionally do not provide substantially any effect. When the present invention is made use of simply as the detoxification method, simple proteins that are directed to obtain, if any, are quire naturally left as such.

In the present specification, the term "essential proteins" of the "innoxious essential proteins" called MIT include conjugated proteins having the essential amino acid type components (such as glycoproteins, nucleoproteins, chromoproteins and phosphoroproteins) and the term "protein derivatives" in the "MIT protein derivatives" includes amino acids derived from the above-mentioned "MIT" (hydrolysis with an acid), amino acid esters (esterification of the amino acids), and amino acid salts (reaction between the amino acids and bases). The term "derived proteins" in the "MIT-derived proteins" includes gelatin, peptide and peptone as the derivative protein formed secondarily from the above-mentioned "essential proteins" by partial hydrolysis and the like.

In the present specification, the heating system represented by the term "oil bath heating" means a heating system which comprises adding oil to fine particles of the raw material, placing them in a heating vessel, heating the vessel from outside and heating the fine particles of the raw material by means of the hot oil. Thus, the material as the object of heating is not exposed to the direct heat but can be heated uniformly and stably at a strictly controlled temperature with a high level of accuracy.

The direct heat agitation type dry-heating employed conventionally causes the temperature difference of as high as 80°–120° C. between the wall exposed to the direct heat and the content or between the wall and the center so that fractioning due to the practical temperature difference is not feasible and involves the critical disadvantage in that the raw material adhering to the wall surface is converted to tar. If the oil bath heating is employed, by contrast, fractioning heating becomes possible for the first time due to the controlled heating. It becomes possible for the first time due to the controlled heating. It becomes possible, for example, to stably heat the material at 204° C.±1° C., thereby eliminating perfectly the formation of the cancerogenic tar.

In the present specification, further, the terms "equipped with", "equipped perfectly with" and "contain" a certain substance A represent not only the case where the substance A is contained as a simple substance but also the case where the substance A is contained as a constituent element of a compound while it has a chemical bond to others.

In the present specification, further, the term "tar" principally denotes the "cancerogenic tar".

What is claimed is:

1. Method of producing an interferon-inducing substance, which comprises comminuting a protein source containing essential amino acids and also containing proteins of hetero-arrangement and being selected from the group consisting of glycoproteins, nucleoproteins, chromoproteins and phosphoroproteins, distributing the thus obtained particulate protein source in oil, uniformly heating the oil mixture at a temperature of 203°–298° C. to denature the protein source into material including the essential amino acids and material including the proteins of hetero-arrangement, and separating said material including the essential amino acids, said material constituting an interferon-inducing substance.

2. Method according to claim 1 wherein the protein source is originally liquid which is dehydrated and solidified prior to being comminuted.

3. Method according to claim 1 wherein the protein source is human blood, human urine, fish, shellfish, snails or soybean.

4. Method according to claim 1 wherein the heating temperature is between 203° and 289° C.

5. Method according to claim 1 wherein the heating temperature is between 203° and 219° C.

6. Method according to claim 1 wherein the heating temperature is between 203° and 206° C.

7. Method according to claim 1 wherein the material including the essential amino acids is recovered by adsorption with starch or active carbon.

* * * * *